United States Patent [19]

Drake et al.

[11] Patent Number: 4,543,673
[45] Date of Patent: Oct. 1, 1985

[54] VAULTED INTRAOCULAR LENS

[75] Inventors: Anthony F. Drake; Fernard J. Masse; Dennis T. Grendahl, all of Santa Barbara, Calif.

[73] Assignee: Surgidev Corporation, Goleta, Calif.

[21] Appl. No.: 500,766

[22] Filed: Jun. 3, 1983

[51] Int. Cl.⁴ .......................... A61F 1/16; A61F 1/24; B29D 11/00
[52] U.S. Cl. ........................................ 623/6; 264/1.7; 264/2.7; 264/339; 425/392; 425/808
[58] Field of Search ....................... 3/13; 264/1.7, 2.7, 264/339; 425/808, 392

[56] References Cited

U.S. PATENT DOCUMENTS

| | | | |
|---|---|---|---|
| 3,418,978 | 12/1968 | Wise et al. | 425/808 X |
| 3,475,521 | 10/1969 | Stroop | 264/1.7 X |
| 4,150,471 | 4/1979 | Richards et al. | 264/1.7 X |
| 4,159,546 | 7/1979 | Shearing | 3/13 |
| 4,426,741 | 1/1984 | Bittner | 3/13 |
| 4,474,355 | 10/1984 | Greshes | 425/808 X |

OTHER PUBLICATIONS

"Planned Extracapsular Cataract Extraction and the Insertion of the Lindstrom Centrex Style 20 Posterior Chamber Lens", by R. L. Lindstrom, Copyright 1981 (Paper), pp. 1–11.
Style 115 Shepard Universal A/C IOL, "One-Size-Fits-All", Advertisement, Americal IOL International, 15542 Graham St., Huntington Beach, CA 92647, 1 page, Dec. 29, 1981.
Model AC/PC-55 Anterior/Posterior Chamber (Pannu), Advertisement, American Medical Optics (4 pages), Jan. 1982.

Primary Examiner—Ronald L. Frinks
Attorney, Agent, or Firm—Hugh D. Jaeger

[57] ABSTRACT

Vaulted intraocular lens including a method and apparatus for vaulting universally an intraocular lens incorporating any geometrical configuration of closed or open loops attached to a lens such as a plano-convex or the like. The vaulted intraocular lens includes a base for each loop with either flat feet or flipped feet. The method of vaulting includes a fixture assembly including a base, a retainer, and a cap, the base and retainer screwing together and encompassing the lens including the plurality of loops, and the cap fitting down through a hole in the retainer providing gravity pressure against the lens and creating the vault. The vaulted lens, as well as the fixture and method of vaulting the lens, lends itself universally to any type of lens using any predetermined geometrically shaped loops, whether the loops be closed loops or open loops.

6 Claims, 10 Drawing Figures

VAULTED INTRAOCULAR LENS

BACKGROUND OF THE INVENTION

1. Field of the Invention

The present invention pertains to surgically implantable intraocular lenses and, more particularly, pertains to vaulted intraocular lenses, the vaulted intraocular lenses including a plurality of loops of predetermined geometrical shape, the lenses being either posterior lenses or anterior chamber lenses.

2. Description of the Prior Art

Prior art intraocular lenses in the past have been manufactured by tedious and archaic methods. Some of the early prior art lenses were manufactured without vaults and then later lenses were manufactured with vaults, but where the vaults would be a standard vault regardless of the diameter such as the Lieb lens.

The most recently manufactured vaulted lenses required a separate form for each lens as manufactured, which required a separate vault fixture. This resulted in considerable expenditures of time and energy, and considerable expenditures of lost time and motion.

With the considerable success of implants of intraocular lenses over the last years and the acceptance by the ophthalmology community, the number of implanted IOL's has increased as well as the demand worldwide. Also, the ophthalmologists have demanded styles based on personal preference involved by the opthalmologists in their own personal techniques in the insertion of the lens as well as the success of lenses as accepted by their patients.

Consequently, manufacturing in optimizing production and meeting the demand of supply of lenses for the ophthalmologists has been difficult in light of the numerous styles as required by the opthalmologists.

The present invention overcomes the disadvantages of the prior art manufacturing methods by providing a universal vault fixture for manufacturing and providing vaults in any style of intraocular lens regardless of the designated anterior or posterior chamber lens and the designated plurality of loops of a predetermined geometrical shape.

SUMMARY OF THE INVENTION

The general purpose of the present invention is to provide a vaulted intraocular lens through a manufacturing method and procedure by utilizing a universal lens vault fixture which can provide a vault in loops including either a flat base or a flipped base, the lens having any plurality of loops extending outward from the lens, and the loops assuming any predetermined geometrical shape. The lens can assume any optical shape, the cap of the vault fixture being accommodating thereto. This includes plano-convex, bi-convex, convex-concave, and other like shapes. The loops of the intraocular lens can either be open loops or closed loops. The number of loops can be one or more, preferably two, three, or four.

According to one embodiment of the present invention, there is provided a vaulted intraocular lens, the intraocular lens including a plurality of loops positioned and extending outward from a lens, the vault provided between the base of a plurality of loops and the lens, where the vault is formed by a universal vault fixture including a base, a retainer, and a cap where the base and the retainer are secured together with the lens and loops inbetween, and the cap fitting through a hole in the retainer and exerting pressure downward against the lens which disposes forward into a hole in the base, and the loops achieving a vault through the pressure exerted by the cap against the surface area of the base. The fixture can be immersed in warm water to provide for easy formation of the vault and the loops, which due to the inherent characteristics of the material utilized maintains a memory of the vault. In this situation it is commonly understood that the material of the lens and the loops would be polymethylmethacrylate (PMMA), but any like material can be utilized.

One significant aspect and feature of the present invention is that the vaulted intraocular lens can be vaulted by the universal vaulting fixture which is utilizable with anterior as well as posterior chamber lenses, any plurality of loops extending outward from the lens, and for any predetermined geometrical shape of the loops.

Another significant aspect and feature of the present invention is a vaulting fixture which is utilizable in a least amount of time and motion, and is universal to any type of intraocular lens with minor variations to the cap for accommodating the lens per se.

A further significant aspect and feature of the present invention is a vaulted intraocular lens which can be utilized with either open-loop lenses or closed-loop lenses, and particularly lends itself in utilization to open-loop lenses as well as closed-loop lenses.

Having thus described one embodiment of the present invention, it is the principal object hereof to provide a vaulted intraocular lens, the universal vault fixture for making the intraocular lenses, and a method of vaulting intraocular lenses.

An object of the present invention is that any intraocular lens incorporating monofilament or the like loops can be easily vaulted, regardless of the complex predetermined geometrical shape of the loops.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF PREFERRED EMBODIMENTS

Figure 1:
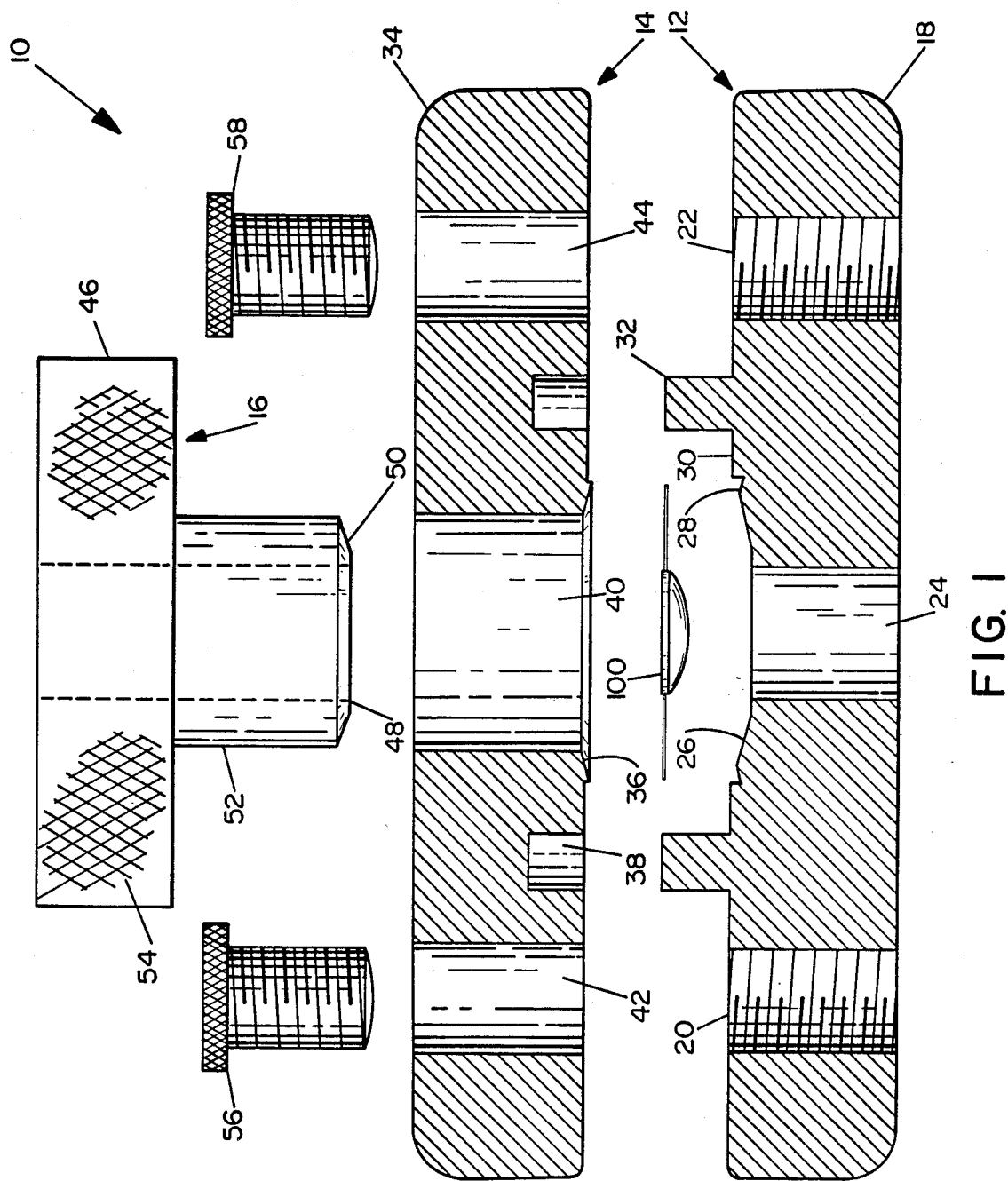
FIG. 1 illustrates a sectional view of a vault fixture including a base, a retainer, and a cap.

FIG. 1, which illustrates a sectional view of a vault intraocular lens fixture 10, includes a base 12, a retainer 14, and a cap 16.

Figure 2:
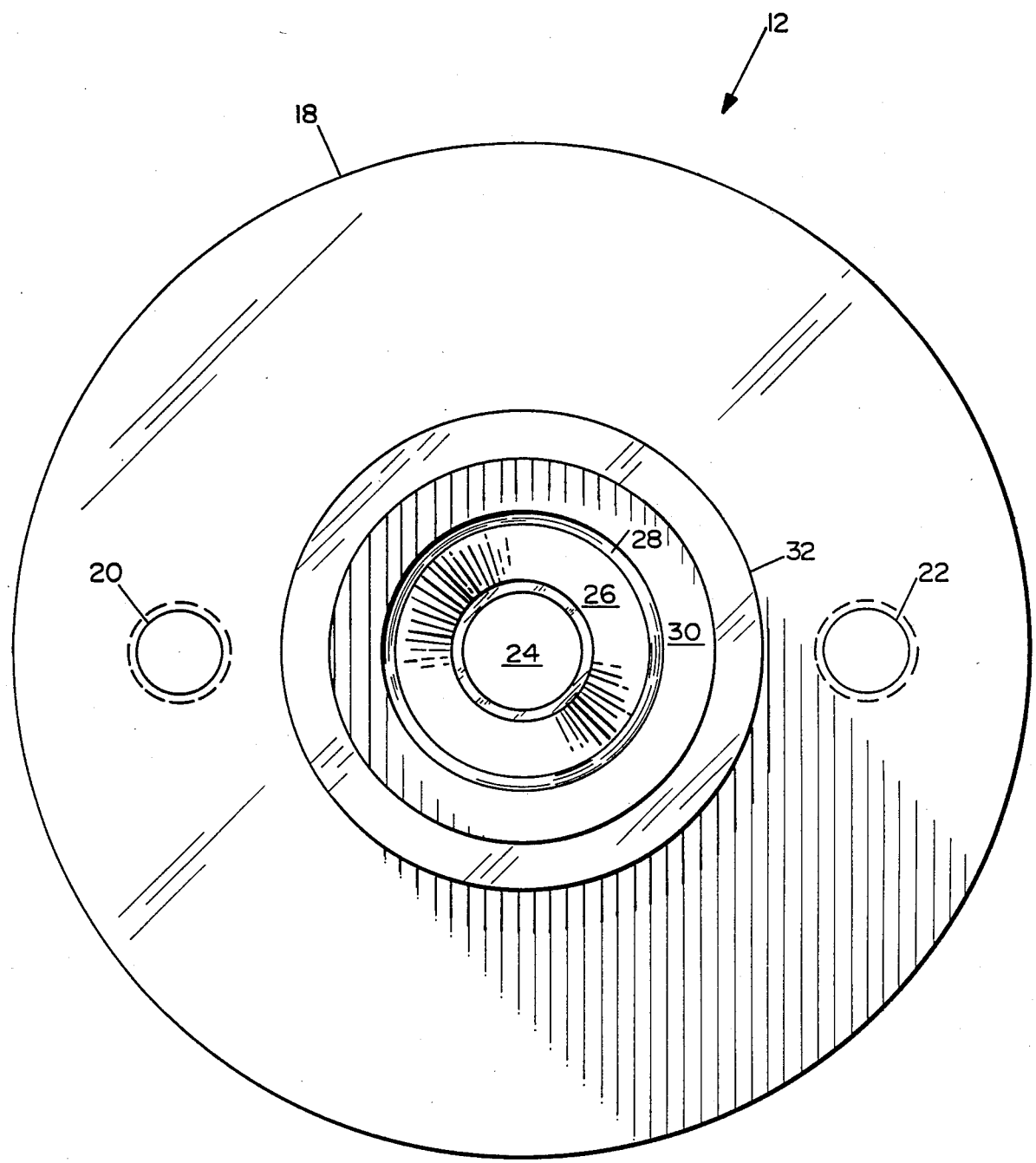
FIG. 2 illustrates a top view of the base.

The base 12 includes a housing 18, two screw holes 20 and 22, a central lens hole 24, a vault portion 26, a flipped base portion 28 which in this instance is shown in a flipped configuration but which can also be illustrated in a flat configuration, by way of example and for purposes of illustration only and not to be construed as limiting of the present invention, a flat portion 30, and an encompassing key 32. Surfaces of the elements 18–30 are also illustrated in FIG. 2.

Figure 3:
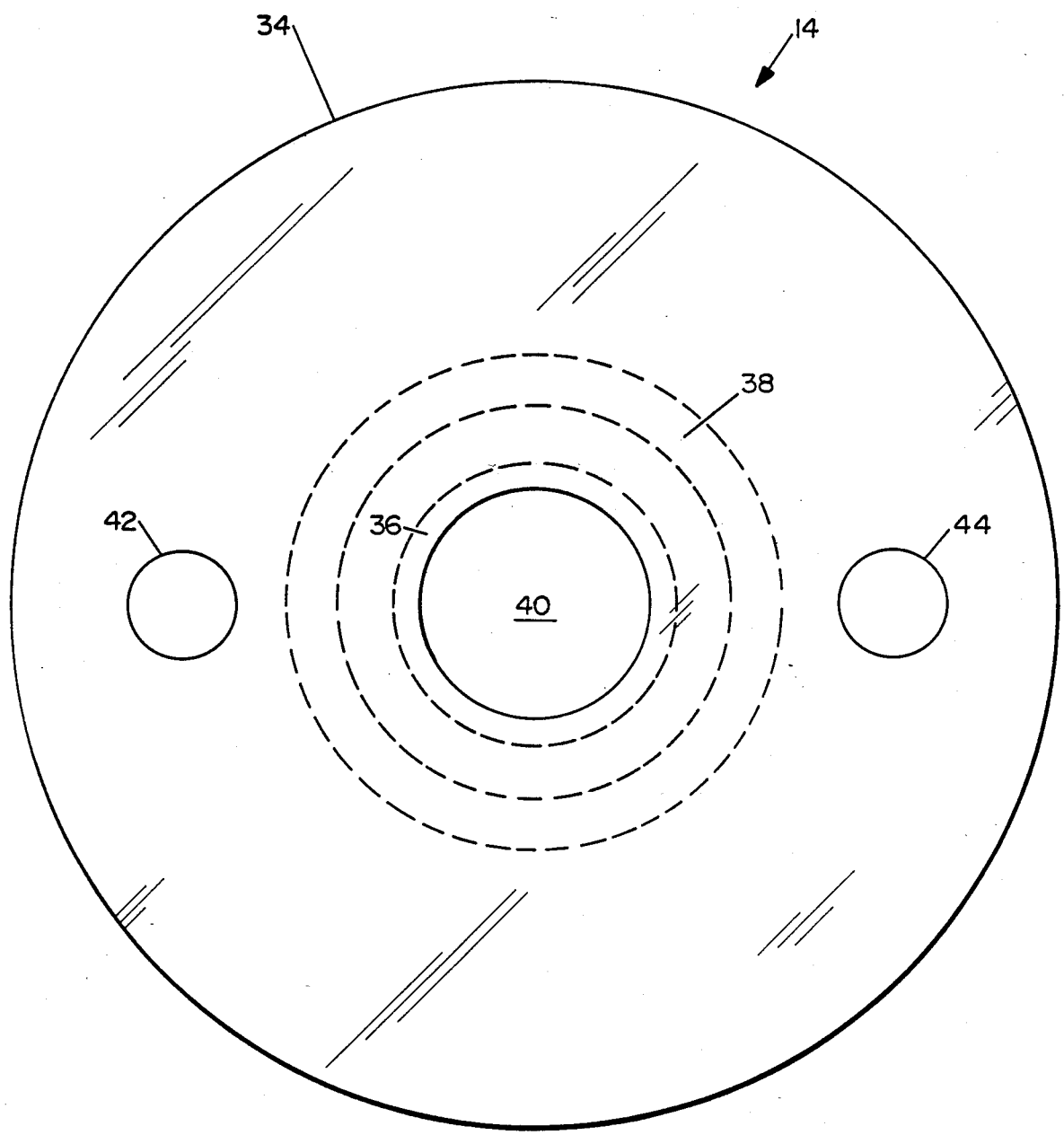
FIG. 3 illustrates a top view of the retainer.

The retainer 14 includes a housing 34, a complementary flat or flipped portion 36, a keyway 38, a cap hole 40 which is central to the housing, and holes 42 and 44. FIG. 3 illustrates a top view of the surfaces of the elements of the retainer 14.

The cap 16 includes a housing 46, a lens hole 48, a vault surface 50, a central cylindrical portion 52 which is corresponding to the cap hole 40 for engagement therein, and a round gripping portion 54.

The base and retainer engage against each other in geometrical relationship with respect to each other while the cap 16 engages down through the retainer 14 to engage against a lens between the base and retainer providing a vault to a lens encompassed therein. Bolts 56 and 58 extend down through the holes to secure the base 12 to the retainer 14.

FIG. 2 illustrates a top view of the base 12 of FIG. 1 where all numerals correspond to those elements previously described.

FIG. 3 illustrates a top view of the retainer 14 of FIG. 1 where all numerals correspond to those elements previously described.

Figure 4:
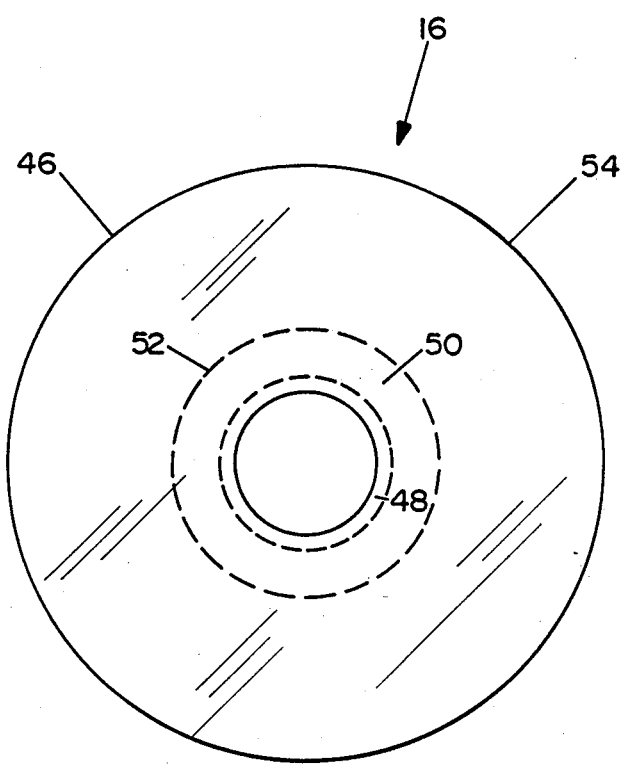
FIG. 4 illustrates a top view of the cap.

FIG. 4 illustrates a top view of the cap 16 of FIG. 1 where all numerals correspond to those elements previously described.

MODE OF OPERATION

The vaulted intraocular lens vault fixture 10 is operated in that an unvaulted lens 100 is positioned in the central part of the base 12. The optic is disposed through the hole 24. The retainer 14 is engaged to the base 12 with the two retaining bolts 56 and 58 with the lens 100 retained therebetween. Two O-rings can facilitate a lens-loop retainer. The unit can then be submersed in a bath of water such as at 76° C. or the like whereupon the cap 16 is positioned through the retainer 14 and the base 12. This action of the cap 16 through gravity causes a downward displacement of the lens 100 by lowering the loops and providing a vault and inherently providing memory through the characteristics of the material for a predetermined vault. The base of the loop can also include a flipped portion as so indicated as provided between surfaces 28 and 36. These surfaces can also provide a respective flat non-flipped base.

The process of vaulting is performed in accordance with the steps as set forth above.

The vaulted intraocular lens fixture particularly lends itself not only to vaulting loops, but also providing a flip in the base.

Figure 5A:
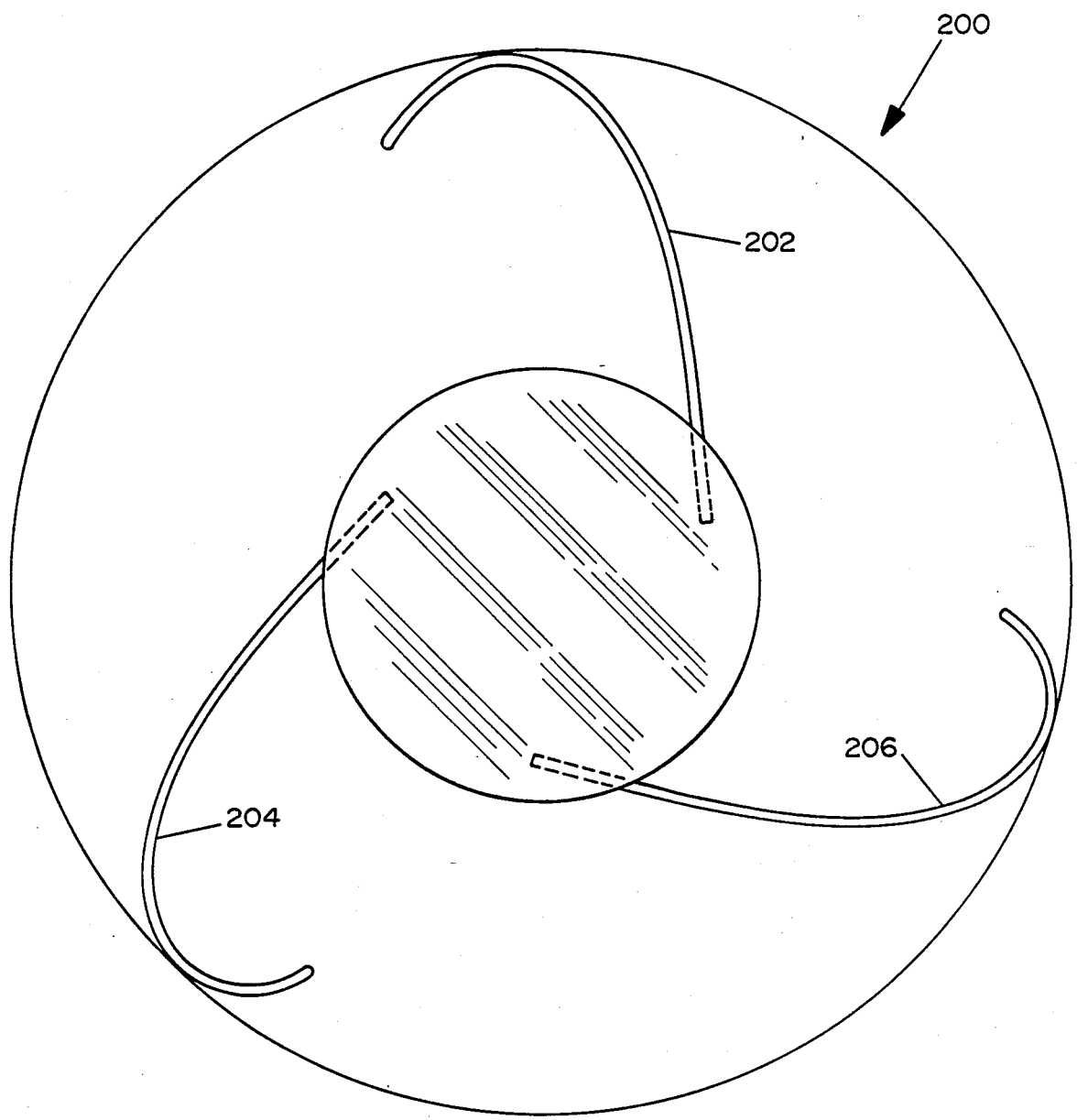
FIGS. 5A and 5B illustrate an intraocular lens having three outwardly extending open and vaulted loops.
Figure 5B:
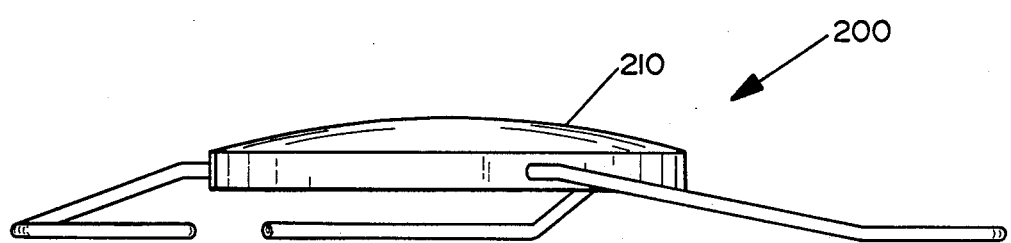

FIG. 5A illustrates a top view and FIG. 5B illustrates a side view of a lens 200 including three loops 202, 204 and 206 with a vault 208 in a plano-convex lens 210 which can be manufactured as a product by the method as previously described in the universal vault fixture 10 for the vaulted intraocular lens.

Figure 6A:
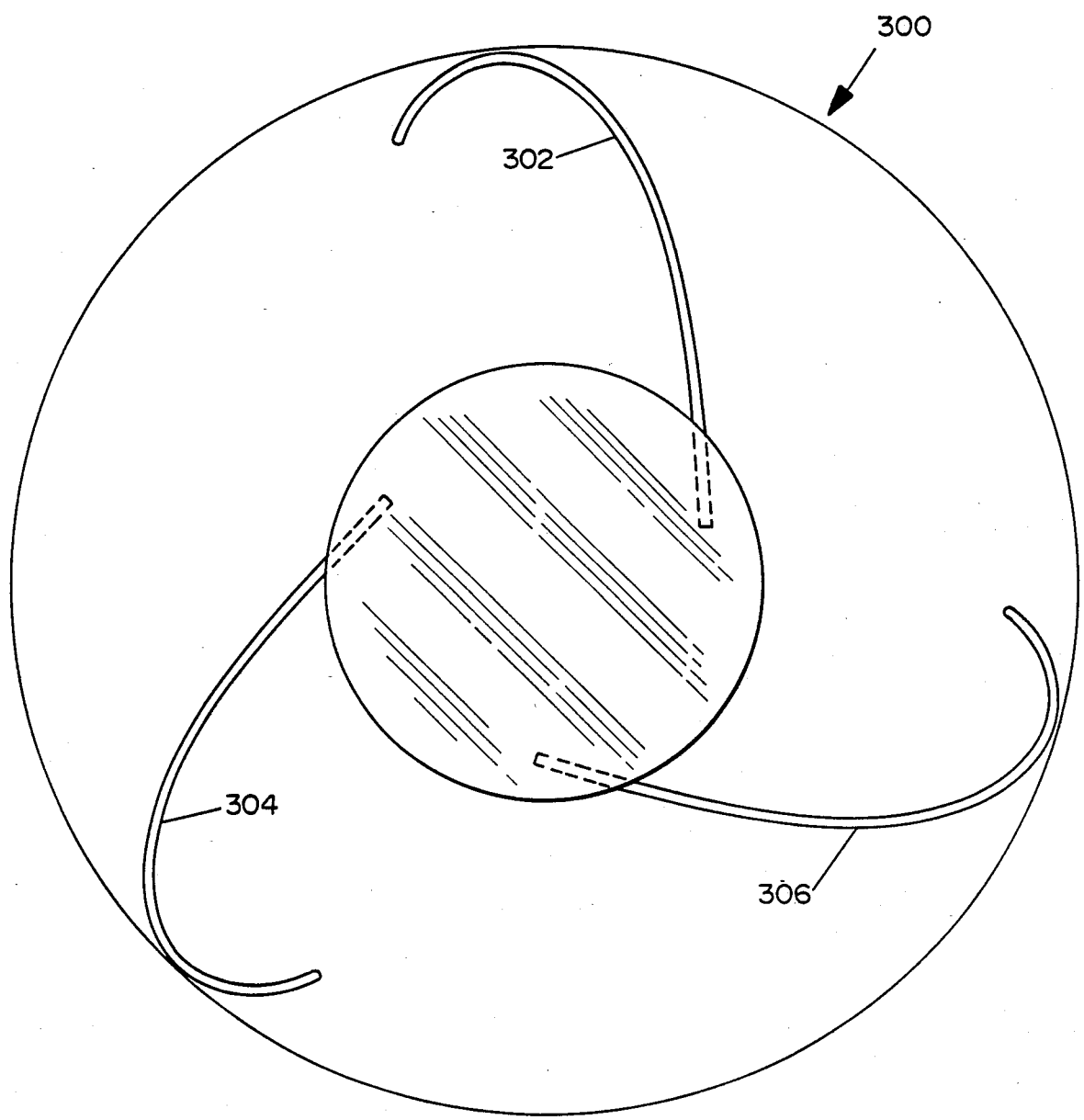
FIGS. 6A and 6B illustrate an intraocular lens having three outwardly extending open and vaulted loops with a flipped loop end; and, FIGS. 7A and 7B illustrate an intraocular lens having four outwardly extending open and vaulted loops with upwardly flipped end members.
Figure 6B:
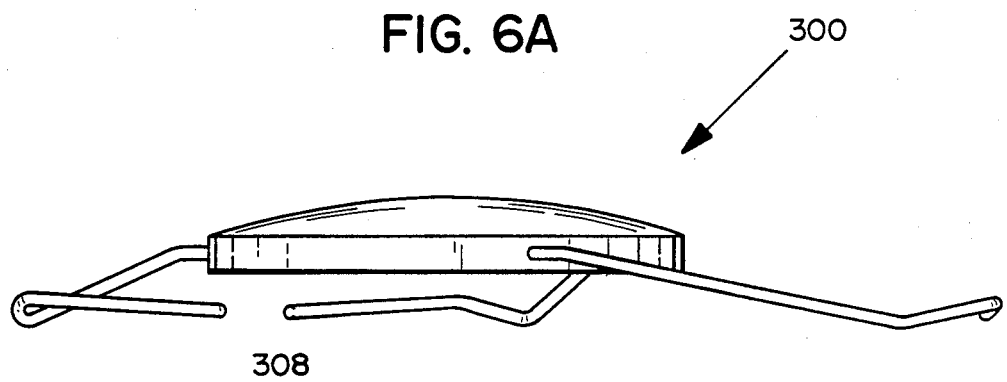

FIG. 6A illustrates a top view and FIG. 6B illustrates a side view of a lens 300 including loops 302, 304, and 306 and a vault 308 manufactured as a product by the process as previously described in the universal fixture 10 for the vaulted intraocular lens.

Figure 7A:
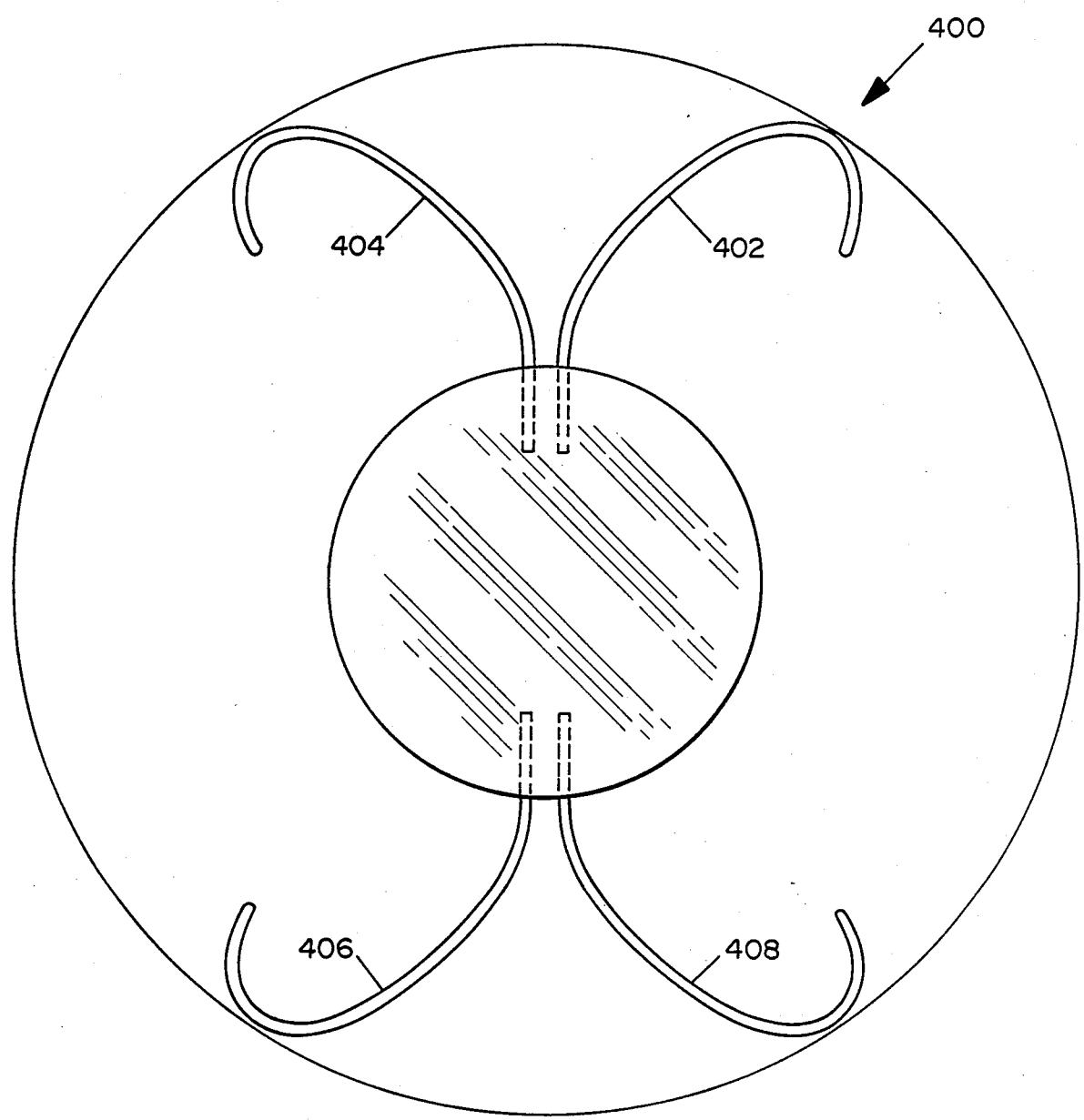
Figure 7B:
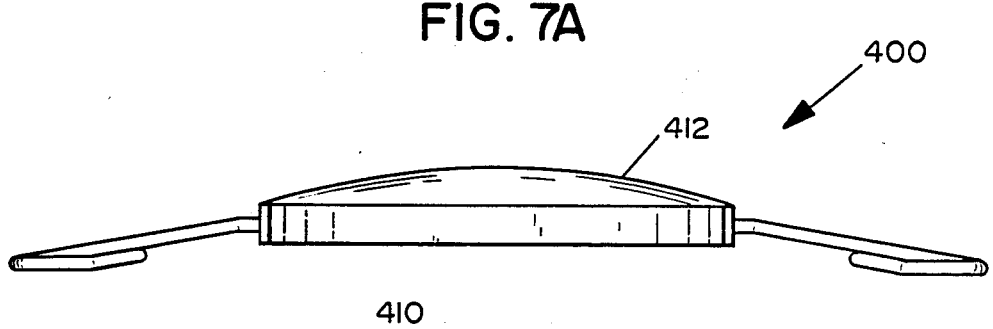

FIG. 7A illustrates a top view and FIG. 7B illustrates a side view of a vaulted intraocular lens 400 including loops 402, 404, 406 and 408 with a vault 410 about a plano-convex lens 412.

Various modifications can be made to the present invention without departing from the apparent scope thereof.

Any type of intraocular lens, whether the lens be an anterior chamber lens or posterior chamber lens, can be provided with a suitable vault regardless of the specific loop geometrical configuration, whether the geometrical configuration be an open loop or a closed loop. The geometrical configurations can be provided in the lens prior to forming the vaults in a planar situation and then the vault and flipped end can be provided accordingly. This will provide a vault in the lens and flipped ends as predetermined.

Having thus described the invention, what is claimed is:

1. Vaulted intraocular lens universal fixture comprising:
   a. base means for supporting a lens and including vault means encompassing therein;
   b. retainer means including a complementary corresponding geometrical vault position with respect to the base means; and,
   c. cap means for protruding down a central hole in said base means and said retainer means for providing a vault against a surface of said base means.

2. Fixture of claim 1 wherein said base means further comprises a flipped means adjacent said vaulting means for flipping ends of loops of said lens.

3. Process for vaulting loops of an intraocular lens comprising the steps of:
   a. supporting an intraocular lens with a plurality of outwardly extending loops on a base, said base including a vaulting surface;
   b. securing a retainer having a complementary corresponding geometrical configuration to said base, said lens secured between said base and said retainer;
   c. supporting a cap down through a hole in said retainer, said cap having a hole for accommodating said lens, said cap also including a vaulting surface for mating with said vaulting surface of said base for providing a vault in said loops;
   d. submersing said fixture of said base, said retainer, and said cap in a bath of hot liquid for a predetermined time interval; and,
   e. separating said retainer and said cap from each other for freeing said lens, whereby said loops of said lens are provided with a predetermined vault.

4. Lens of three outwardly extending open and vaulted loops by the process of claim 3.

5. Lens of three outwardly extending open and vaulted loops, each of said loops including a flipped loop end by the process of claim 4.

6. Lens of four outwardly extending open and vaulted loops, each of said loops including an upwardly flipped end member by the process of claim 4.

* * * * *